(12) United States Patent
Durgin et al.

(10) Patent No.: US 6,610,056 B2
(45) Date of Patent: Aug. 26, 2003

(54) MULTI-FUNCTION SURGICAL INSTRUMENT

(75) Inventors: Russell F. Durgin, Attleboro, MA (US); Sheila Caira, Auburndale, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 42 days.

(21) Appl. No.: 09/784,118

(22) Filed: Feb. 22, 2001

(65) Prior Publication Data

US 2001/0009985 A1 Jul. 26, 2001

Related U.S. Application Data

(62) Division of application No. 09/178,570, filed on Oct. 26, 1998, now Pat. No. 6,221,039.

(51) Int. Cl.[7] .............................................. A61B 18/18
(52) U.S. Cl. .......................................... 606/41; 606/50
(58) Field of Search ............................. 606/41, 45, 46, 606/47, 48, 49, 50, 20, 21

(56) References Cited

U.S. PATENT DOCUMENTS

| | | | | |
|---|---|---|---|---|
| 4,532,924 A | * | 8/1985 | Auth et al. ................... 606/50 |
| 5,336,222 A | * | 8/1994 | Durgin et al. ................. 606/50 |
| 5,462,521 A | * | 10/1995 | Brucker et al. ............... 604/20 |
| 5,500,012 A | * | 3/1996 | Brucker et al. ............. 607/122 |
| 5,507,744 A | * | 4/1996 | Tay et al. ...................... 606/50 |
| 5,578,031 A | * | 11/1996 | Wilk et al. .................... 606/49 |
| 6,010,512 A | * | 1/2000 | Chu et al. .................... 606/113 |
| 6,106,524 A | * | 8/2000 | Eggers et al. ................. 606/50 |

* cited by examiner

Primary Examiner—Michael Peffley
(74) Attorney, Agent, or Firm—Kenyon & Kenyon

(57) ABSTRACT

A multi-function surgical instrument is disclosed. In accordance with an embodiment of the present invention, the surgical instrument includes a catheter, a bipolar hemostat assembly, an attachment member, and a surgical tool. The bipolar hemostat assembly includes an electrical connector at a proximal end, a bipolar electrode assembly at a distal end, and first and second electrical leads extending from the proximal end to the distal end and disposed within the catheter. The bipolar electrode assembly includes an aperture that extends axially therethrough. The attachment member is disposed within the catheter and has a proximal end and a distal end where the distal end is movable within the aperture of the bipolar electrode assembly between a first position wherein the distal end is extended from the bipolar electrode assembly and a second position wherein the distal end is retracted within the bipolar electrode assembly. The surgical tool is attached to the distal end of the attachment member.

10 Claims, 15 Drawing Sheets

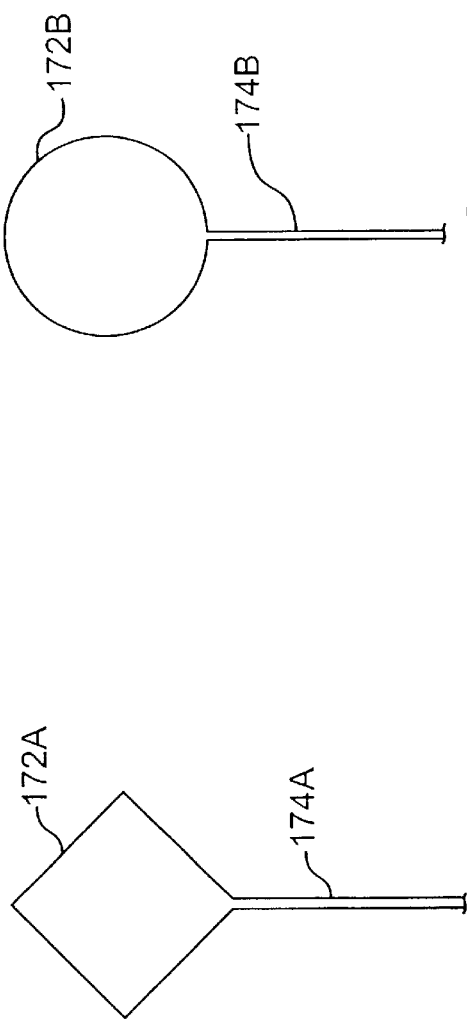
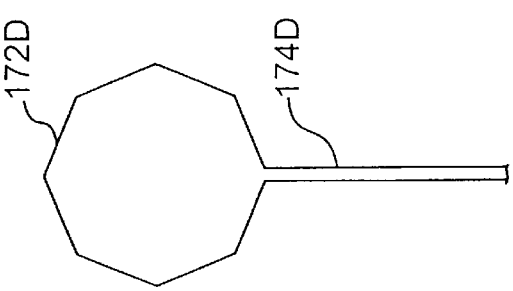
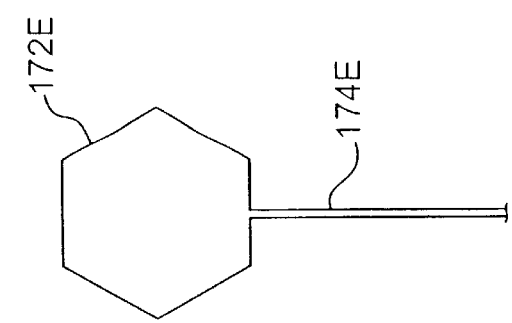
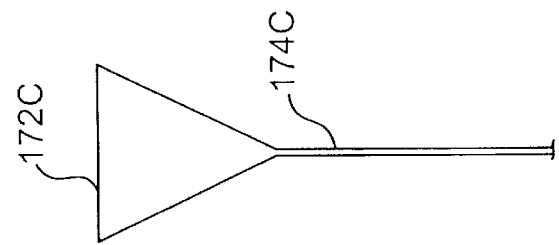
FIG. 6
FIG. 7
FIG. 8
FIG. 9
FIG. 10

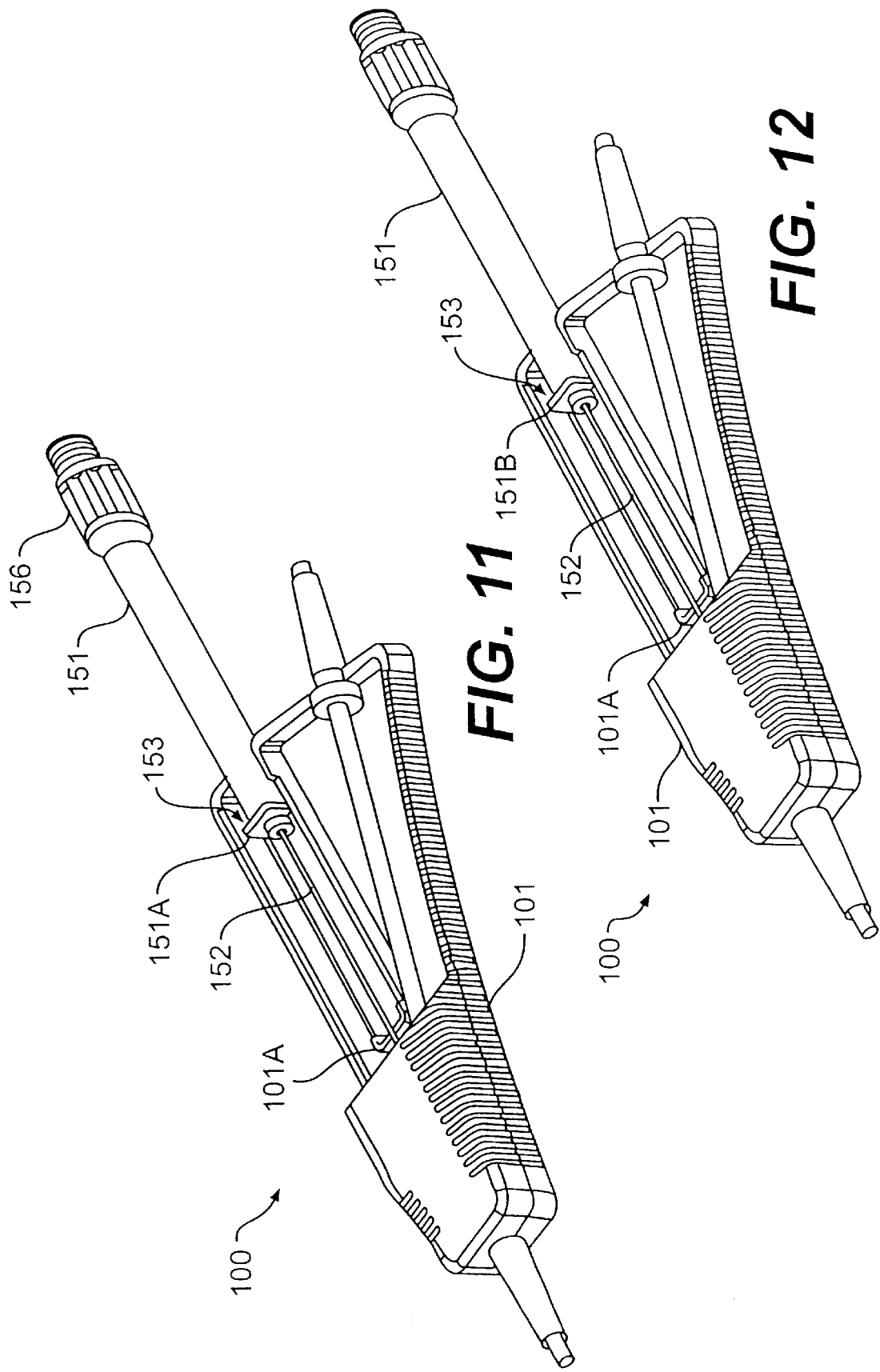

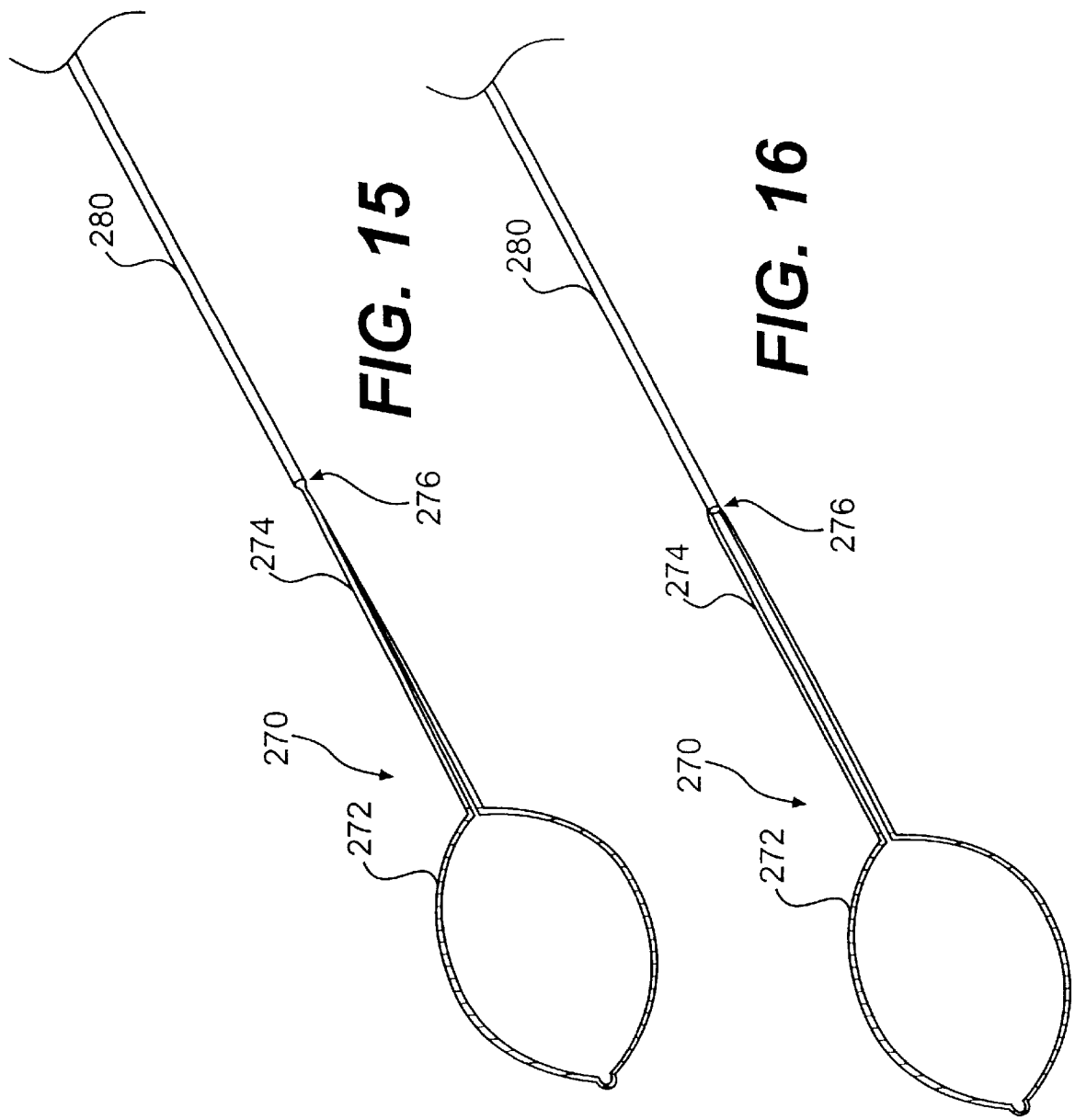

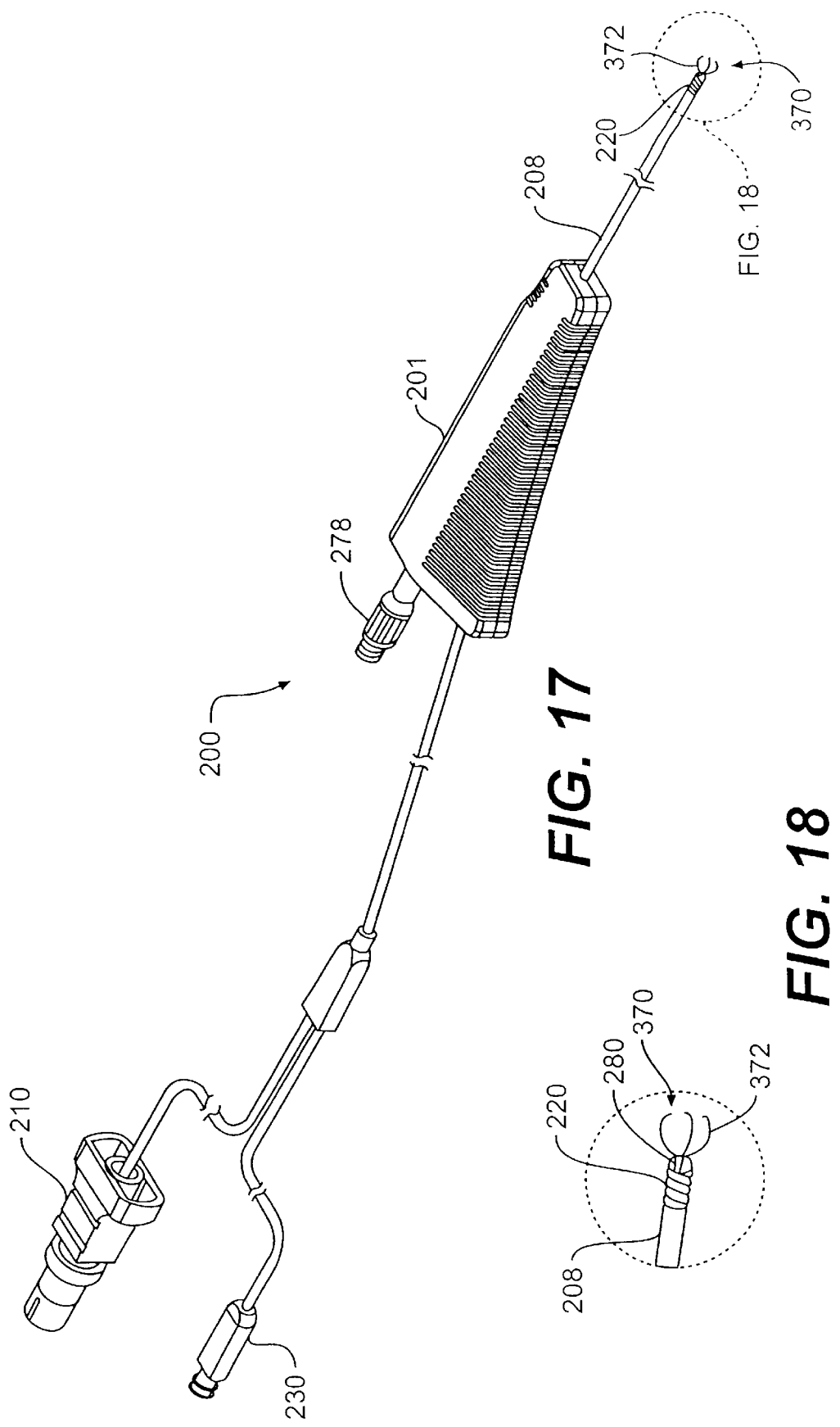

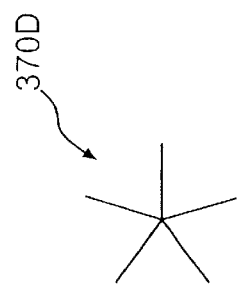
FIG. 23
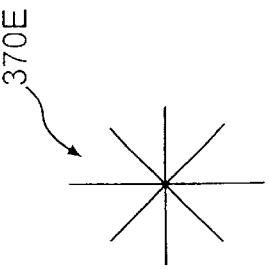
FIG. 24
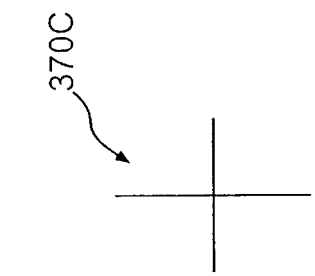
FIG. 22
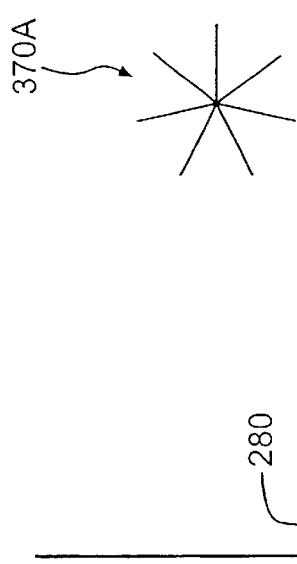
FIG. 20
FIG. 21
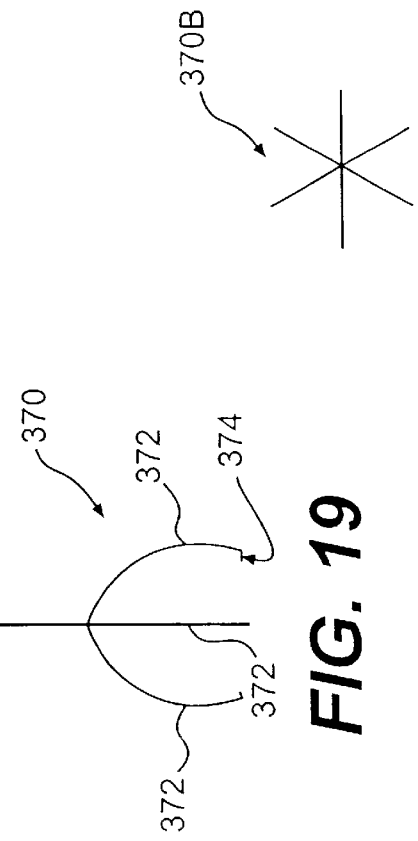
FIG. 19

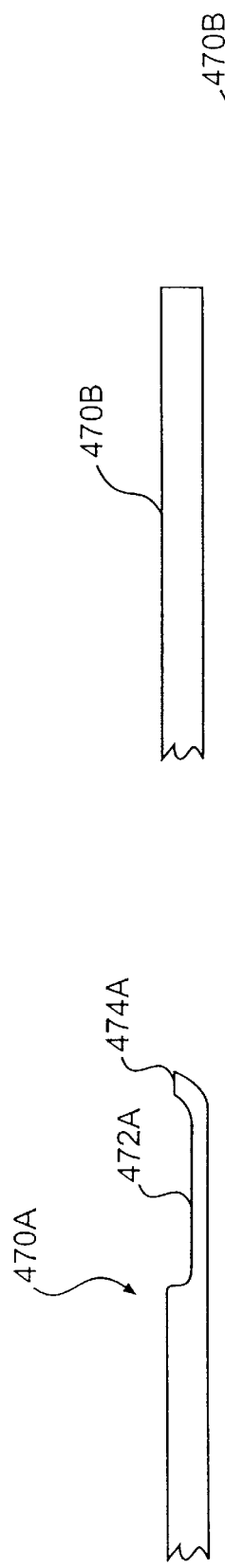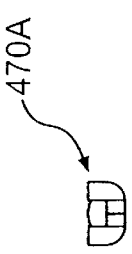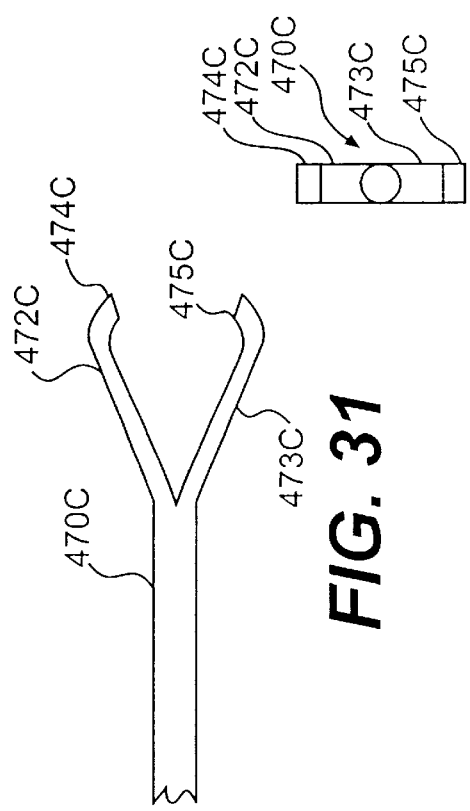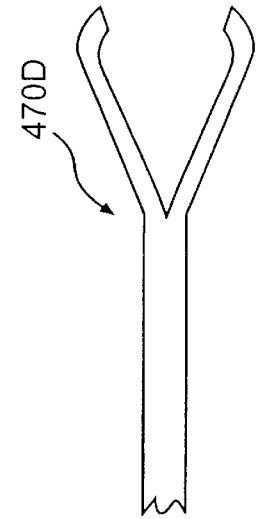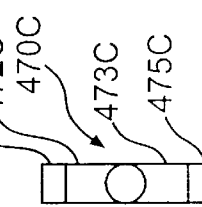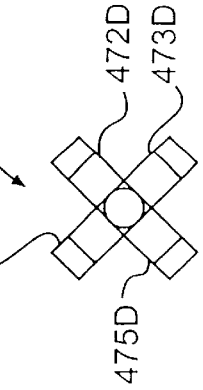

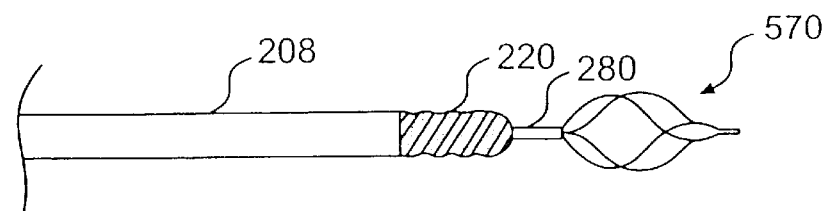
FIG. 35
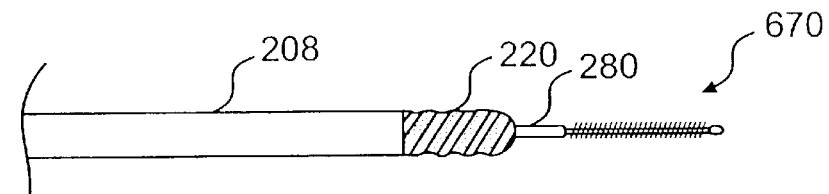
FIG. 36
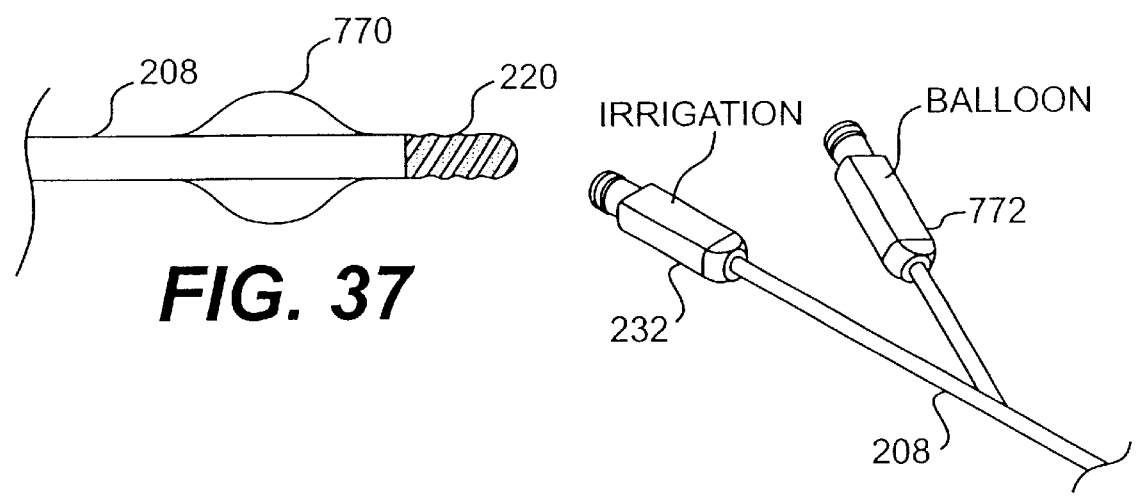
FIG. 37
FIG. 38
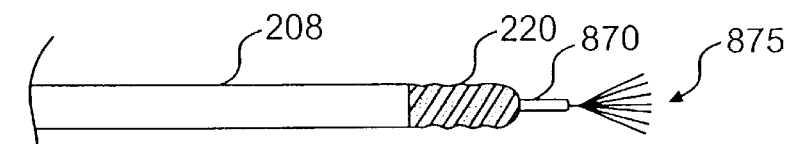
FIG. 39

MULTI-FUNCTION SURGICAL INSTRUMENT

This is a division of U.S. patent application Ser. No. 09/178,570, filed Oct. 26, 1998 now U.S. Pat. No. 6,221,039.

BACKGROUND OF THE INVENTION

The present invention relates to a multi-function surgical instrument. More specifically, the invention is a surgical instrument that combines a hemostat assembly with other surgical tools to provide the capability to a surgeon to accomplish multiple surgical procedures with a single instrument.

Currently, a surgical instrument is known that combines a hemostatic capability with an irrigation capability and an injection capability. The instrument provides multi-functionality in a single surgical instrument, which results in efficiencies for the surgeon who is performing a surgical procedure. With the known multi-function surgical instrument, the surgeon is not required to insert and remove multiple surgical instruments from the patient in order to perform the procedure. However, there are procedures that the surgeon may be required to perform that require capabilities in addition to, or different from, those capabilities provided by the multi-function instrument described above. For example, the surgeon may be required to capture a polyp by utilizing a snare device. In this circumstance where the physician is required to perform a procedure that requires a capability that is not included in the multi-function surgical instrument described above, the physician would have to utilize a separate tool in order to obtain this capability. This reduces the efficiency of the surgeon when performing the entire procedure.

Therefore, it would be desirable to provide a multi-function surgical instrument that could provide other capabilities to the surgeon, in combination with a hemostatic capability, in a single surgical instrument.

SUMMARY OF THE INVENTION

In accordance with an embodiment of the present invention, a multi-function surgical instrument is provided. The surgical instrument includes a catheter, a bipolar hemostat assembly, an attachment member, and a surgical tool. The bipolar hemostat assembly includes an electrical connector at a proximal end, a bipolar electrode assembly at a distal end, and first and second electrical leads extending from the proximal end to the distal end and disposed within the catheter. The bipolar electrode assembly includes an aperture that extends axially therethrough. The attachment member is disposed within the catheter and has a proximal end and a distal end where the distal end is movable within the aperture of the bipolar electrode assembly between a first position wherein the distal end is extended from the bipolar electrode assembly and a second position wherein the distal end is retracted within the bipolar electrode assembly. The surgical tool is attached to the distal end of the attachment member.

BRIEF DESCRIPTION OF THE DRAWINGS

FIG. 6 illustrates a second embodiment for the geometric configuration for a snare loop of the present invention.

FIG. 7 illustrates a third embodiment for the geometric configuration for a snare loop of the present invention.

FIG. 8 illustrates a fourth embodiment for the geometric configuration for a snare loop of the present invention.

FIG. 9 illustrates a fifth embodiment for the geometric configuration for a snare loop of the present invention.

FIG. 10 illustrates a sixth embodiment for the geometric configuration for a snare loop of the present invention.

FIG. 11 illustrates an alternative embodiment for the multi-function surgical instrument of the present invention where the needle hub is restrained against rotation.

FIG. 12 illustrates an alternative embodiment for the multi-function surgical instrument of the present invention where the needle hub is rotatable.

FIG. 15 illustrates a first embodiment for the attachment of the snare to the attachment member for the embodiment of the instrument of FIG. 13.

FIG. 16 illustrates a second embodiment for the attachment of the snare to the attachment member for the embodiment of the instrument of FIG. 13.

FIG. 17 illustrates an alternative embodiment for the multi-function surgical instrument of the present invention where a grasper/forceps device is attached to a support member.

FIG. 18 is a view of the distal end of the instrument of FIG. 17.

FIG. 19 illustrates an embodiment of a configuration for a grasper/forceps device of the present invention.

FIG. 20 illustrates a second embodiment for the configuration for the grasper/forceps device of the present invention.

FIG. 21 illustrates a third embodiment for the configuration for the grasper/forceps device of the present invention.

FIG. 22 illustrates a fourth embodiment for the configuration for the grasper/forceps device of the present invention.

FIG. 23 illustrates a fifth embodiment for the configuration for the grasper/forceps device of the present invention.

FIG. 24 illustrates a sixth embodiment for the configuration for a grasper/forceps device of the present invention.

FIG. 27 illustrates an embodiment of a configuration for a scraper/forceps device of the present invention.

FIG. 28 is a front view of the scraper/forceps device of FIG. 27.

FIG. 29 illustrates a second embodiment for the configuration for the scraper/forceps device of the present invention.

FIG. 30 is a front view of the scraper/forceps device of FIG. 29.

FIG. 31 illustrates a third embodiment for the configuration for the scraper/forceps device of the present invention.

FIG. 32 is a front view of the scraper/forceps device of FIG. 31.

FIG. 33 illustrates a fourth embodiment for the configuration for the scraper/forceps device of the present invention.

FIG. 34 is a front view of the scraper/forceps device of FIG. 33.

FIG. 35 illustrates an alternative embodiment for the multi-function surgical instrument of the present invention where a retrieval basket is attached to a support member.

FIG. 36 illustrates an alternative embodiment for the multi-function surgical instrument of the present invention where a cytology brush is attached to a support member.

FIG. 37 illustrates an alternative embodiment for the multi-function surgical instrument of the present invention where a balloon has been added to the outside diameter of the catheter.

FIG. 38 illustrates a balloon hub that could be attached to the catheter for use with the surgical instrument of FIG. 37.

FIG. 39 illustrates an alternative embodiment for the multi-function surgical instrument of the present invention where the shaft comprises a cryotherapy tube.

DETAILED DESCRIPTION

Figure 1:
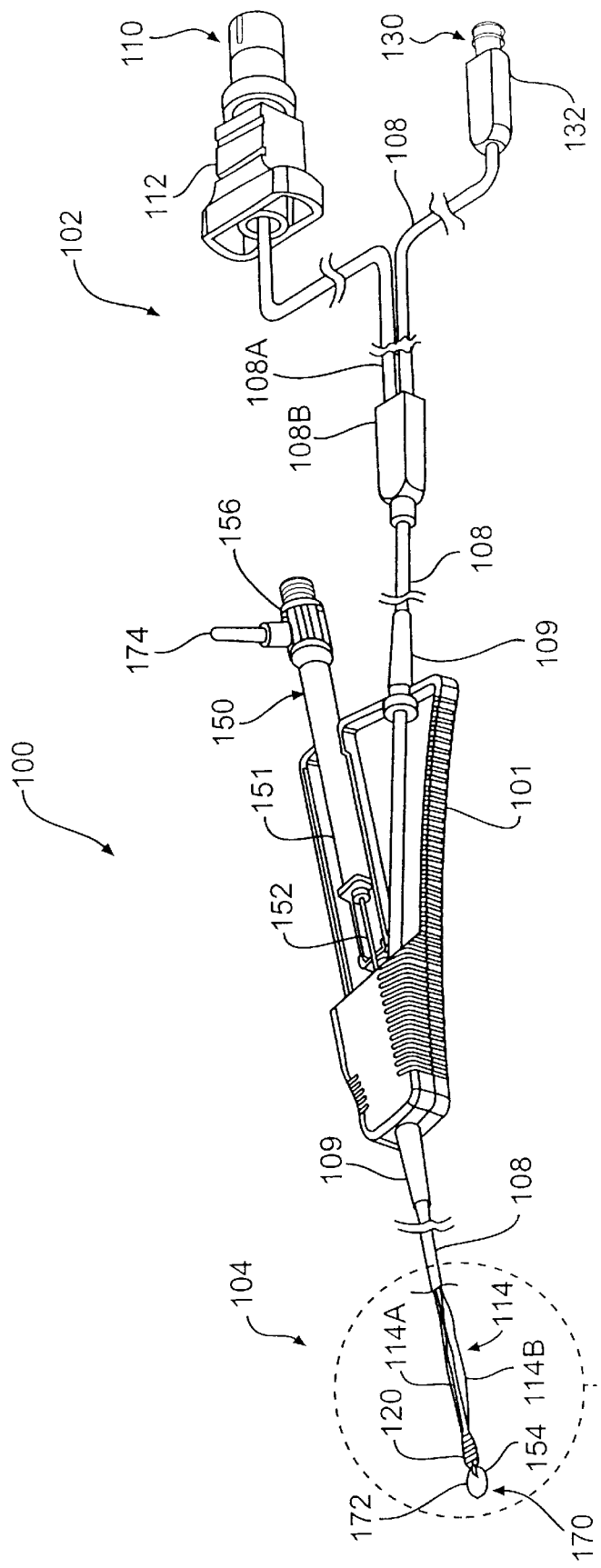
FIG. 1 illustrates a first embodiment for a multi-function surgical instrument in accordance with the present invention.

FIG. 1 illustrates a first embodiment for the multi-function surgical instrument 100 in accordance with the present invention. As can be seen in FIG. 1, surgical instrument 100 includes a bipolar hemostat assembly 110, an irrigation assembly 130, and a needle assembly 150.

Figure 2:
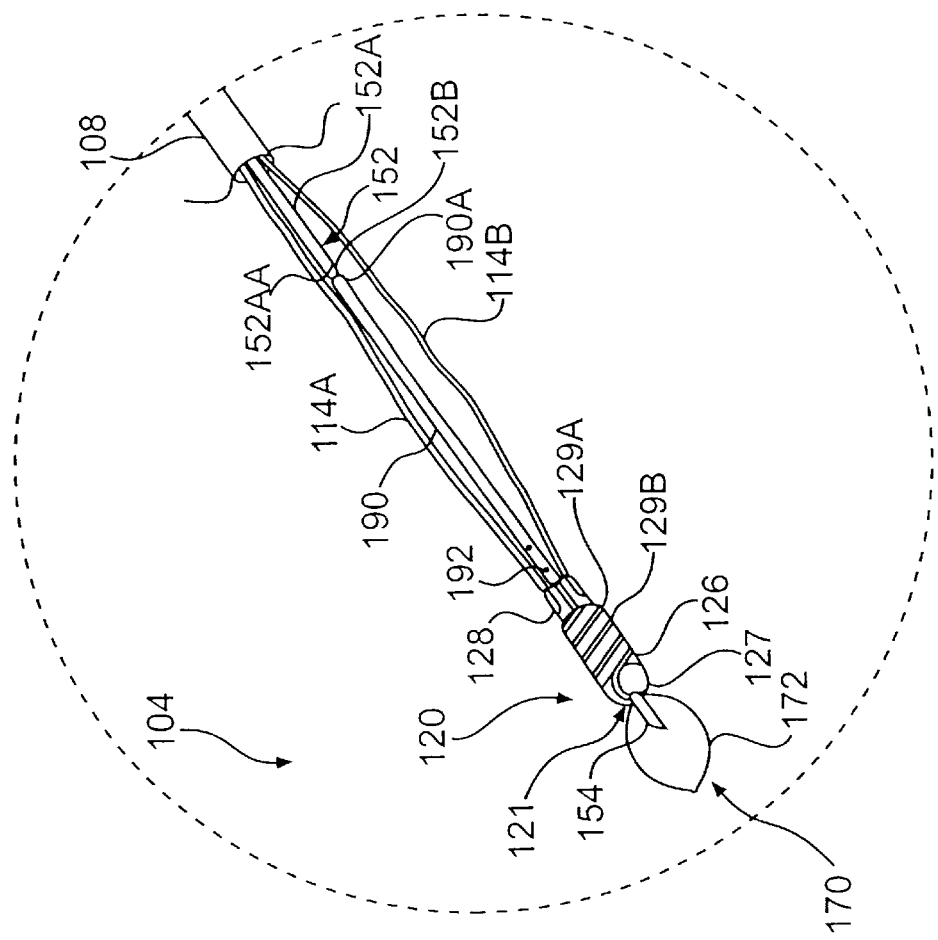
FIG. 2 is a view of the distal end of the surgical instrument of FIG. 1.

Bipolar hemostat assembly 110 includes an RF generator connector 112, electrical leads 114, and a bipolar electrode assembly 120. RF generator connector 112 is located at a proximal end 102 of the multi-function surgical instrument 100 and is utilized to provide connection to an RF generator (not shown) in accordance with well-known principles. Electrical leads 114 extend from RF generator connector 112 through the surgical instrument 100 and terminate at the bipolar electrode assembly 120, which is located at the distal end 104 of the surgical instrument 100. As such, an electrical current can be provided from RF generator connector 112 to the bipolar electrode assembly 120 through electrical leads 114. Electrical leads 114 extend from RF generator connector 112 through extension tube 108A. The electrical leads 114 pass through the catheter hub, or bifurcation, 108B and enter the catheter main shaft 108 of the surgical instrument 100. The electrical leads 114 pass through the catheter main shaft 108 which extends through body 101 of surgical instrument 100 and terminate at bipolar electrode assembly 120. As can be seen in FIGS. 1 and 2, and as will be described further later in this specification, electrical leads 114 consist of a first lead 114A and second lead 114B. As such, in accordance with well-known principles, the bipolar electrode assembly 120, when energized by an electrical current through leads 114, provides hemostatic therapy to a patient.

Irrigation assembly 130 includes an irrigation hub 132. Irrigation hub 132 is attached to catheter main shaft 108, which passes through catheter hub 108B. Irrigation hub 132 is provided to attach to an irrigation pump (not shown in FIG. 1). The irrigation pump would provide fluid to irrigation hub 132 where the fluid would pass through the catheter main shaft 108 through the length of surgical instrument 100. The fluid passes through a central lumen 121 (not visible in FIG. 1) that is included in bipolar electrode assembly 120 to be delivered to a site within the body of a patient. Thus, through irrigation assembly 130, fluid to irrigate a site within a patient's body can be provided by surgical instrument 100.

The electrical leads 114 of the bipolar hemostat assembly 110 and the irrigation fluid provided by the irrigation assembly 130 both pass through the catheter main shaft 108. As such, the electrical leads 114 are insulated conductors such that they are electrically isolated from the irrigation fluid that is carried through catheter main shaft 108.

Catheter hub, or bifurcation, 108B contains an internal seal that is provided to prevent irrigation fluid from the irrigation assembly 130 from traveling proximally along surgical instrument 100 through extension tube 108A. Thus, irrigation fluid is able to be pass through catheter main shaft 108, however, the irrigation fluid is not able to "back flow" through extension tube 108A and contact RF connector 112.

The multi-function surgical instrument 100 also contains needle assembly 150. Needle assembly 150 includes an injection needle 152 and is utilized to inject a fluid into a site within the patient's body. As can be seen in FIG. 1, needle assembly 150 includes injection needle 152, needle hub 151, and needle operator 156. Injection needle 152 extends at its proximal end from needle hub 151 through body 101 of surgical instrument 100. Needle 152 extends through catheter main shaft 108 and is received within the central lumen 121 of the bipolar electrode assembly 120. Needle operator 156 is utilized to provide injection fluid to needle assembly 150 for delivery to the patient through needle 152. Needle hub 151, which carries needle 152 at its distal end, is slidably mounted within body 101 of surgical instrument 100 such that needle 152 may be moved distally through bipolar electrode assembly 120 such that the injection needle tip 154 extends externally from the bipolar electrode assembly 120. Needle hub 151 is also able to be moved in a proximal direction with respect to body 101 such that injection needle tip 154 is able to be retracted within lumen 121 of bipolar electrode assembly 120. The user of surgical instrument 100 is able to grip needle hub 151 at the needle operator 156 in order to move needle assembly 150 both distally and proximally along body 101.

Body 101 contains a seal that surrounds catheter main shaft 108, which passes therethrough. Needle 152, as it passes through body 101, penetrates the seal that surrounds the main shaft 108 and the wall of the main shaft 108 to extend through main shaft 108 to the distal end 104 of surgical instrument 100. The seal is provided in body 101 and around main shaft 108 to prevent the irrigation fluid that is also carried in main shaft 108 from exiting the shaft and body 101 at the location where needle 152 penetrates the main shaft 108. Body 101 also includes strain relief members 109. Strain relief members 109 are disposed on body 101 and are used to attach catheter 108 to body 101 at the proximal and distal ends of body 101.

FIG. 2 provides a more detailed view of the distal end 104 of the surgical instrument 100 so that the configuration of the injection needle 152, electrical leads 114A, 114B, and bipolar electrode assembly 120 can be more clearly seen. In order to provide this more detailed view of the distal end 104 of the surgical instrument 100, a portion of main shaft 108 has been cut away such that the components referred to above may be more clearly visualized.

As can be seen in FIG. 2, bipolar electrode assembly 120 consist of a cylindrical body portion 126, a hemispherical distal end tip 127 and a shank portion 128. Discrete spiral electrodes 129A and 129B are disposed on the outer surface of the cylindrical body portion 126 and the hemispherical distal end tip 127. Each of the spiral electrodes 129A and 129B connect to one of the electrical leads 114A and 114B.

As can be visualized in FIG. 2, bipolar electrode assembly 120 contains a lumen 121 that extends centrally and axially therethrough and which receives injection needle 152 within it. As can be seen in FIG. 2, injection needle tip 154 has been extended from bipolar electrode assembly 120. Bipolar electrode assembly 120 is a gold plated ceramic tip and each electrical lead 114A and 114B is connected to a different one of the spiral electrodes 129A, 129B with a conductive epoxy.

As can be further seen in FIG. 2, injection needle 152 extends through catheter 108 and may be comprised of two portions. In the embodiment of FIG. 2, injection needle 152 consists of a 22 gauge hypotube 152A into which is welded a 25 gauge needle 152B at the distal end 152AA of the hypotube 152A. The 25 gauge needle 152B is received within a guide tube 190 which extends proximally from shank portion 128 of the bipolar electrode assembly 120. Guide tube 190 defines a lumen which is axially aligned with lumen 121 that is included in bipolar electrode assembly 120. Guide tube 190 serves to guide injection needle 152 into the bipolar electrode assembly 120 and also acts as a positive stop which allows for the needle to only extend a predetermined length beyond the hemispherical distal end tip 127 of bipolar electrode assembly 120. This stop feature is accomplished by utilizing the structures of the distal end 152AA of hypotube 152A and the proximal end 190A of guide tube 190. As can be understood, as injection needle 152 is moved distally within catheter 108 and is received within guide tube 190, eventually the distal end 152AA of hypotube 152A will abut the proximal end 190A of guide tube 190 such that the injection needle 152 can not be inserted any further within guide tube 190. This interaction of the hypotube 152A and the guide tube 190 serves as a positive stop for limiting the distance that injection needle 152 can be extended from the surgical instrument 100.

As can be also seen in FIG. 2, guide tube 190 also includes a plurality of holes 192 that extend completely through the wall structure of guide tube 190. The purpose of the holes 192 in guide tube 190 is to permit the irrigation fluid that is carried through catheter 108 to flow through the guide tube from outside of the guide tube such that it is able to enter and pass through lumen 121 in bipolar electrode assembly 120 for delivery to the body of the patient. The guide tube 190 can be attached to the bipolar electrode assembly 120 through any of a variety of methods, one of which is by utilizing an epoxy to secure the tube to the electrode assembly.

A multi-function surgical instrument that includes a hemostat capability, an irrigation capability, and an injection needle capability is disclosed in U.S. Pat. Nos. 5,336,222 and 5,522,815 and the two above-referenced patents are incorporated herein in their entirety.

In returning to FIGS. 1 and 2, it can also be seen that multi-function surgical instrument 100 includes a snare device 170. As will be described in more detail later in this specification, snare 170 is directly attached to injection needle 152 and can be extended from, and retracted into, bipolar electrode assembly 120 by moving needle 152 distally and proximally, respectively, within bipolar electrode assembly 120. Snare 170 includes a snare loop 172 that can be deployed in an operative configuration when the injection needle 152 has been extended from bipolar electrode assembly 120. The snare loop 172 can be retracted into the bipolar electrode assembly 120 by retracting needle 152 within the bipolar electrode assembly 120. Thus, the operation of snare 170 is controlled by the operator through movement of needle assembly 150. Since the snare 170 is directly attached to injection needle 152, as the injection needle is extended from the bipolar electrode assembly 120 the snare loop 172 will be deployed from the bipolar electrode assembly 120 and as the needle 152 is retracted into the bipolar electrode assembly 120 the snare loop 172 will also be retracted within the bipolar electrode assembly 120.

Snare 170 is utilized to perform a procedure on a patient in accordance with well-known principles. For example, a polyp that is to be removed from a patient can be captured within snare loop 172. As such, snare 170 can be either an electrically energized snare or a non-electrical snare. With either embodiment, snare 170 can be utilized to capture tissue within the body of a patient.

FIGS. 1 and 2 illustrate snare 170 as a monopolar snare wire. As such, a snare electrical connector 174 is provided at the proximal end 102 of surgical instrument 100 on needle operator 156. An electrical lead (not visible) extends from snare electrical connector 174 to snare loop 172 to carry an electrical current from an RF generator (not shown) through electrical connector 174 to snare loop 172. The electrical lead passes from electrical connector 174 to snare loop 172 through catheter main shaft 108 and thus is insulated such that it is electrically isolated from the irrigation fluid that also passes through catheter main shaft 108.

FIGS. 1 and 2 illustrate snare 170 in a first position where snare loop 172 has been deployed from the bipolar electrode assembly 120. As such, needle hub 151 has been moved distally along body portion 101 of the surgical instrument 100. Since the snare is directly attached to the injection needle 152, this distal movement of needle hub 151 will deploy snare loop 172 from the bipolar electrode assembly 120.

Figure 3:
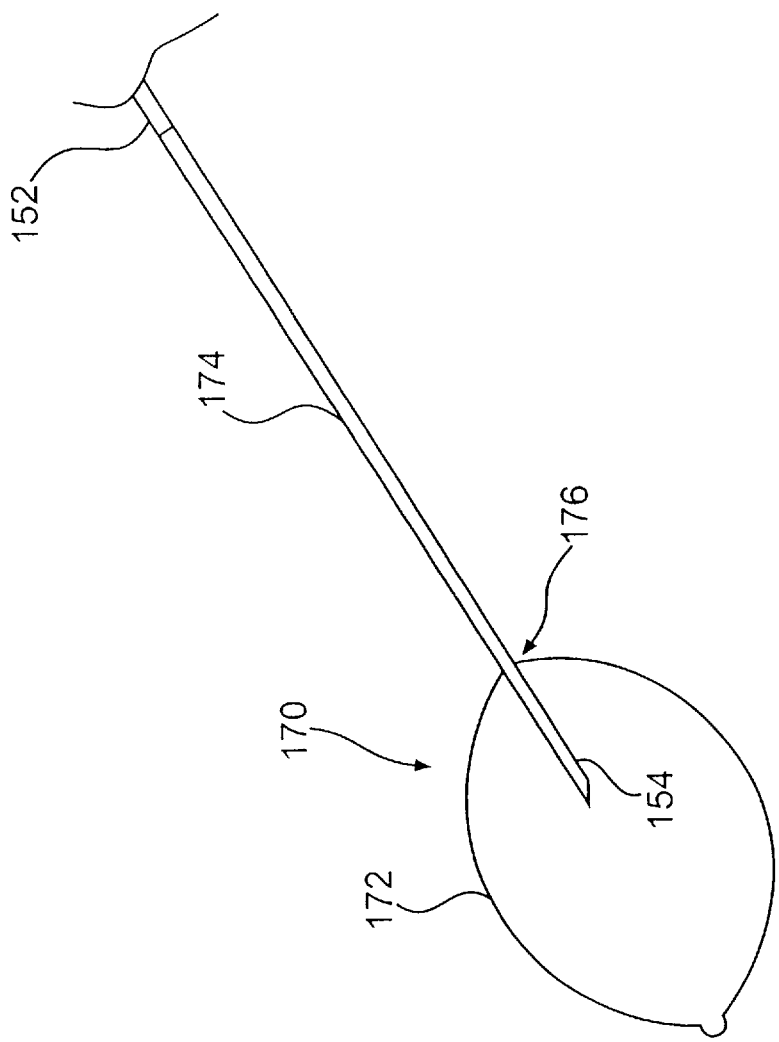
FIG. 3 illustrates an embodiment for the configuration of the attachment between the snare and injection needle.

FIG. 3 illustrates a configuration for the attachment between snare 170 and injection needle 152. As can be seen, snare 170 is comprised of a snare loop 172 and a snare attachment portion 174. In the configuration of FIG. 3, snare loop 172 is an elliptical-shaped loop, however, as will be explained further later in this specification, snare loop 172 can be formed in any of a variety of different geometric shapes. Attachment portion 174 is utilized to attach snare 170 to injection needle 152. The attachment of snare 170 to injection needle 152 extends from attachment point 176 at a distal end of injection needle 152 in a proximal direction along injection needle 152. Attachment point 176 is located a sufficient distance in a proximal direction from needle tip 154 such that the snare loop 172 does not impede the use of needle tip 154 for injecting fluid into the body of a patient. The distance between the distal end of the needle tip 154 and attachment point 176 is not rigidly defined, however, as described above, the distance is sufficient to permit operation of both the snare 170 and the injection needle 152. Additionally, the attachment portion 174 of snare 170 can extend any distance along injection needle 152. A design consideration in determining the length of attachment portion 174 is to provide sufficient strength for the attachment between snare 170 and injection needle 152 such that snare 170 can be utilized for its intended purposes without detaching from injection needle 152.

As discussed previously, snare 170 can either be an electrically energized snare or a non-energized snare and, as such, snare 170 can be manufactured from a variety of materials. For example, snare 170 can be manufactured from Nitinol, stainless steel or other metals, composites, or rigid polymers. The snare loop may be either a single strand wire or a multi-stranded, braided, or twisted wire. Likewise, injection needle 152 may be manufactured from a variety of materials including metals or plastics. As such, the method of attachment between snare 170 and injection needle 152 is in-part dependent upon the materials that are utilized to form snare 170 and injection needle 152. However, the present invention is not limited to any particular method of attaching snare 170 to injection needle 152. As discussed above, depending upon the materials that are utilized to manufacture each of the snare 170 and injection needle 152, the snare 170 could be attached to needle 152 through soldering, welding, swaging, crimping, or by utilizing an adhesive.

Figure 4:
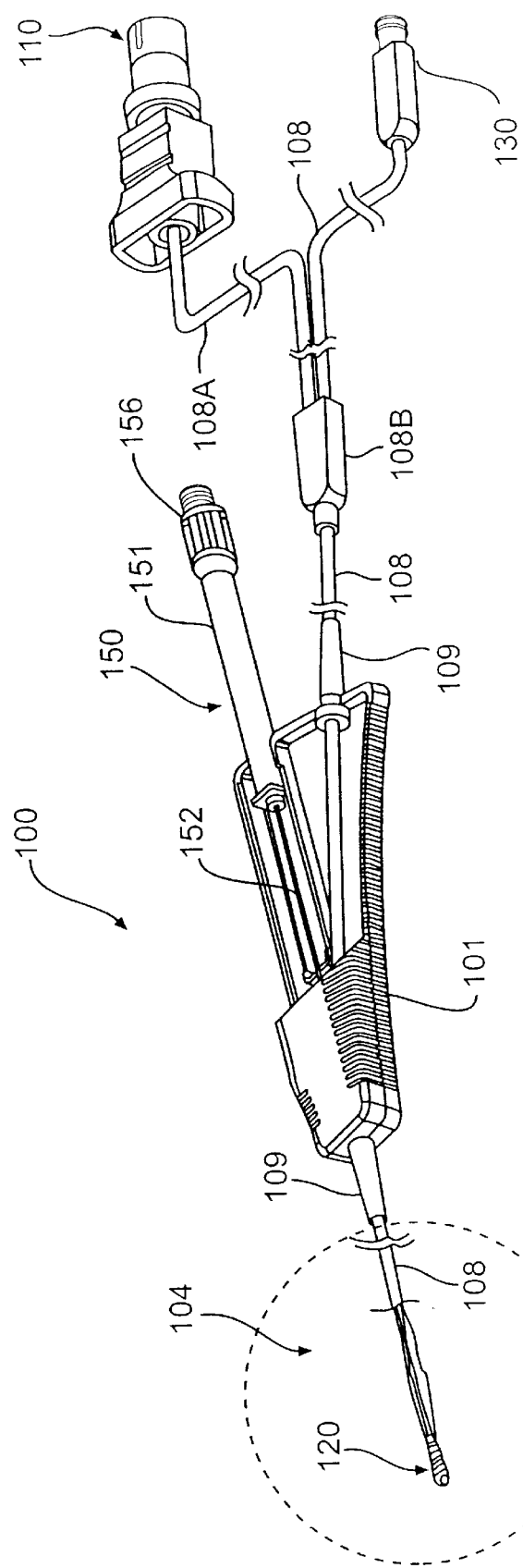
FIG. 4 illustrates the surgical instrument of FIG. 1 in a second position where the snare has been retracted within the bipolar electrode assembly.
Figure 5:
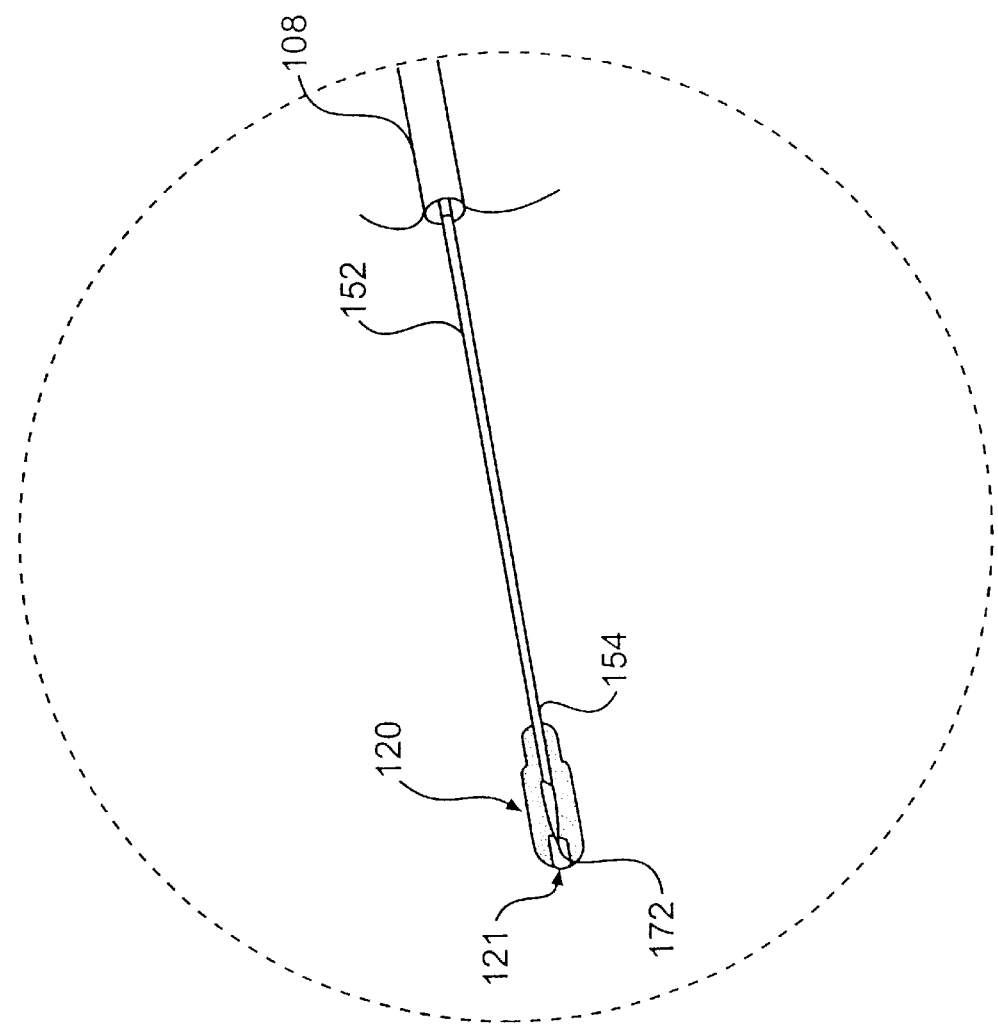
FIG. 5 is a view of a distal end of a surgical instrument in the second position where the snare has been retracted within the bipolar electrode assembly.

FIGS. 4 and 5 illustrate surgical instrument 100 in a second position where snare 170 has been retracted within bipolar electrode assembly 120. As can be seen, needle hub 151 has now been moved proximally along body 101 of surgical instrument 100. This proximal movement of needle hub 151 will also move needle 152 proximally within catheter main shaft 108 which will retract injection needle tip 154 within bipolar electrode assembly 120. Again, since snare 170 is attached to injection needle 152, retraction of injection needle 152 within bipolar electrode assembly 120 will also retract snare loop 172 of snare 170 within the bipolar electrode assembly such that the snare loop 172 is not now in an operative position at the distal end 104 of surgical instrument 100.

As can be seen in greater detail in FIG. 5, the retraction of injection needle 152 has caused snare loop 172 to collapse and be received within lumen 121 of bipolar electrode assembly 120. It is understood that injection needle 152 must be retracted within bipolar electrode assembly 120 a sufficient distance if snare loop 172 is to be entirely received within lumen 121 of the bipolar electrode assembly 120.

As was mentioned previously, snare loop 172 of snare 170 can be formed in any of a variety of geometric configurations. FIGS. 6–10 illustrate several of the alternative embodiments for the geometric configuration for the snare loop of the present invention. As can be seen in FIG. 6, snare loop 172A is configured in a four-sided diamond-shaped configuration. Attachment portion 174A extends from the snare loop 172A for attachment to an injection needle as described previously. FIG. 7 illustrates a circular snare loop 172B attached to a snare attachment portion 174B. FIGS. 8, 9, and 10 illustrate triangular snare loop 172C, an octagonally-configured snare loop 172D, and a six-sided snare loop 172E, respectively. Snare loops 172C, 172D, and 172E are formed with snare attachment portions 174C, 174D, and 174E, respectively. As was mentioned previously for elliptical snare loop 172 for snare 170, the snare loops and snare attachment portions illustrated in FIGS. 6–10 may be formed from any of a variety of materials previously described and contemplated by those skilled in the art and may be attached to an injection needle by any of the methods previously described or by any method contemplated by one skilled in the art.

FIG. 11 illustrates an embodiment for the multi-function surgical instrument 100 where the needle hub 151 can be prevented from rotation about its longitudinal axis within body 101 of the surgical instrument 100. Surgical instrument 100, as illustrated in FIGS. 11 and 12, does not show the bipolar hemostat assembly 110, irrigation assembly 130, and snare 170 as discussed previously, however, those assemblies could be incorporated into the embodiment of the instruments of FIGS. 11 and 12 and their illustration is not required for purposes of describing the features to be discussed in FIGS. 11 and 12.

As mentioned above, the embodiment of surgical tool 100 in FIG. 11 is capable of preventing rotation of needle hub 151. As such, needle hub 151 includes anti-rotation structure 151A at a distal end 153 of needle hub 151. The anti-rotation structure 151A is a flat, planar member that is formed in either a square or rectangular shape. This structure is received within needle hub receiving structure 101A which is included on body 101 of the surgical instrument 100. As the needle hub 151 is moved distally along body 101 in order to extend the injection needle from the distal end of the surgical instrument, the anti-rotation structure 151A is received within the needle hub receiving structure 101A. As can be understood, when the anti-rotation structure 151A is received within the needle hub receiving structure 101A, due to the complimentary structural configuration of the two structures, the needle hub 151 is not able to be rotated when it is in this position on body 101.

FIG. 12 illustrates an embodiment for surgical instrument 100 where the needle hub 151 is able to be rotated about its longitudinal axis within body 101. In order to provide for rotation of needle hub 151 within body 101, a structure 151B with rounded edges is provided at the distal end 153 of needle hub 151. When the rounded structure 151B is received within needle hub receiving structure 101A, because it has rounded corners, the needle hub 151 may be rotated even when it is in its distal-most position on body 101. It may be desirable to provide for rotation of needle hub 151 so that the physician utilizing the surgical instrument 100 may position injection needle 152 and snare 170, which would be attached to needle 152 as described previously, into any position that may be helpful to the surgeon in performing a procedure with the surgical instrument.

Figure 13:
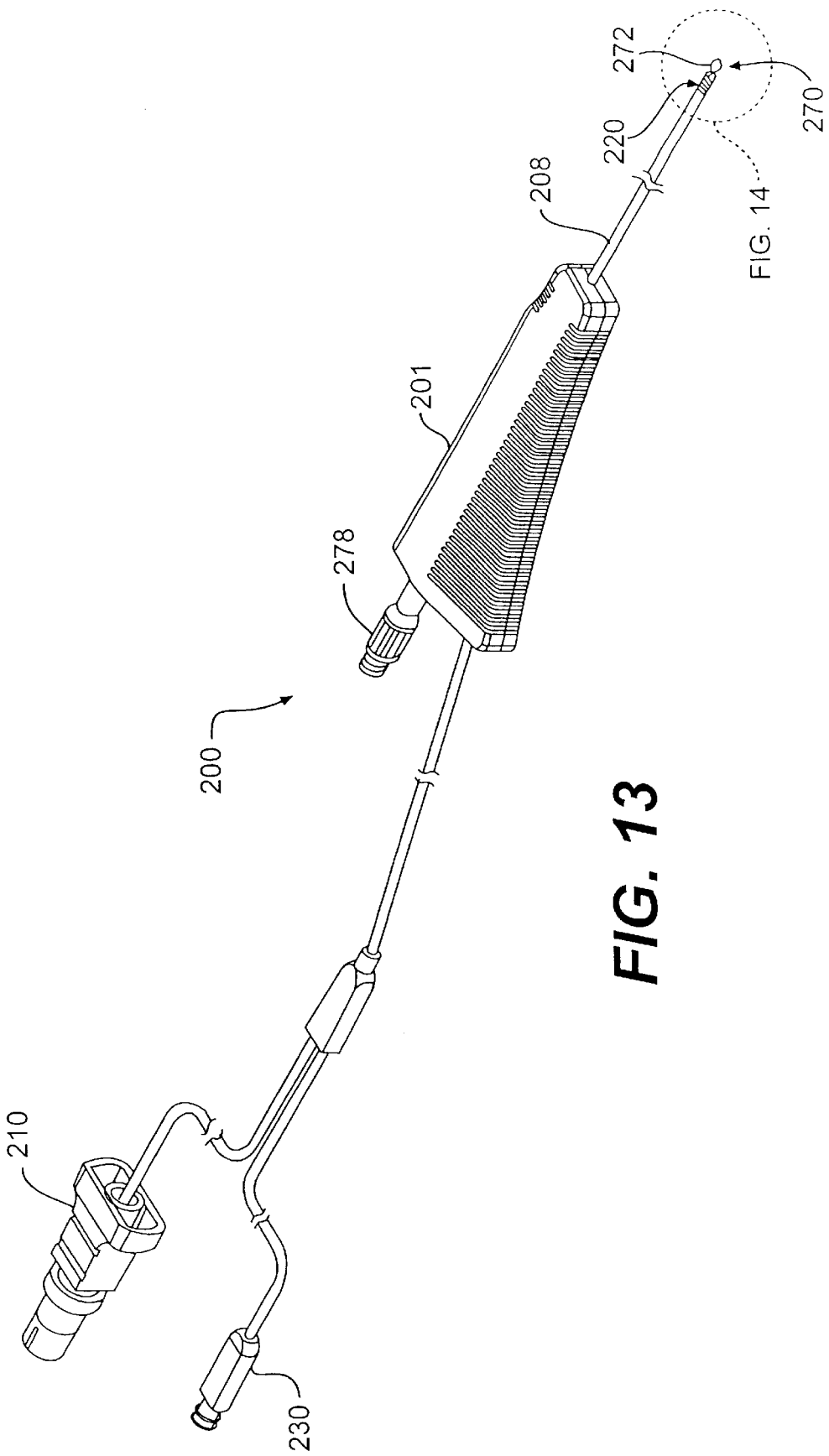
FIG. 13 illustrates an alternative embodiment for the multi-function surgical instrument of the present invention where the snare is attached to an attachment member.
Figure 14:
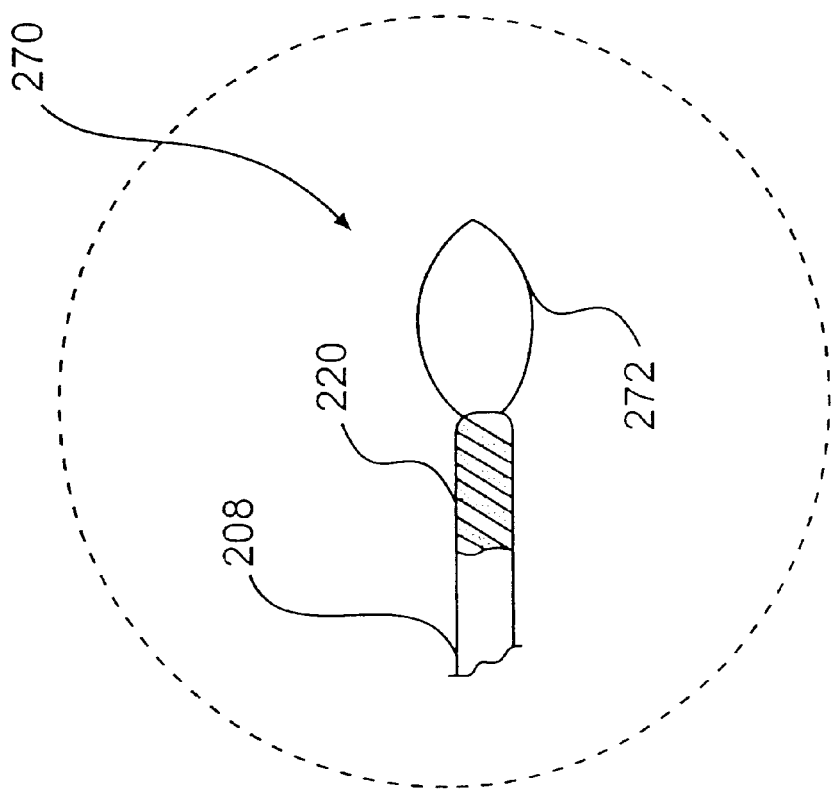
FIG. 14 is a view of the distal end of the instrument of FIG. 13.

It has been described previously that an injection needle could be provided within surgical instrument 100 such that an injection capability was provided to surgical instrument 100. As was also described previously, a snare could be attached to the distal end of the injection needle to provide a snare capability to the surgical instrument. However, it is not required that a needle be utilized with a surgical instrument in order to provide a snare capability to the surgical instrument. FIGS. 13 and 14 illustrate an embodiment for a multi-function surgical instrument 200 that has a hemostat capability, an irrigation capability and a snare capability, without requiring an injection capability.

As can be seen in FIG. 13, multi-function surgical instrument 200 includes a bipolar hemostat assembly 210 and an irrigation assembly 230, which operate in accordance with the principles described previously for the embodiment of surgical instrument 100. FIG. 13 also illustrates a snare 270 that is included in surgical instrument 200. However, in the embodiment of FIGS. 13 and 14 for surgical instrument 200, snare 270 is not attached to an injection needle, but rather, is attached to the distal end of an attachment member (not visible in FIG. 13 and 14) that extends through body 201 of surgical instrument 200 and through catheter 208. The attachment member extends through a central lumen that is included in the bipolar electrode assembly 220, as was described previously for the bipolar electrode assembly 120 in the embodiment of FIG. 1.

As can be seen in FIGS. 15 and 16, snare 270 is attached to attachment member, or support member or shaft, 280 at the distal end of shaft 280. As such, snare loop 272 of snare 270 can be extended from, and retracted into, bipolar electrode assembly 220 by a user gripping operator 278 and moving the attachment member 280 within catheter 208 of surgical tool 200. Thus, adding the functionality of a snare device to a multi-function surgical instrument is not dependent upon including an injection capability in the surgical instrument. The surgical instrument 200 can be provided with a rod or attachment member that extends through the catheter 208 which includes the snare 270 attached at its distal end. By retracting the distal end of the attachment member 280 within the bipolar electrode assembly 220, the snare loop 272 of snare 270 would also be retracted into bipolar electrode assembly 220. By extending attachment member 280 distally from bipolar electrode assembly 220, the snare loop 272 of snare 270 is deployed from the distal end of surgical instrument 200.

FIGS. 15 and 16 illustrate the attachment of snare 270 to attachment member, or shaft, 280. In the embodiment of FIGS. 15 and 16, shaft 280 is illustrated as a hypotube. In FIG. 15, shaft attachment portion 274 of snare 270 has been inserted into shaft 280 and in FIG. 16 shaft attachment portion 274 has been attached to the outer circumference of shaft 280. Snare 270 can be fixed to shaft 280 by utilizing any of a variety of attachment methods and snare 270 and shaft 280 can be formed from any of a variety of materials. For example, snare 270 could be joined to shaft 280 by soldering, welding, swaging, crimping, or utilizing an adhesive. Additionally, snare loop 272 of snare 270 can be configured in any of the geometric shapes as was described previously in FIGS. 6–10.

FIGS. 17 and 18 illustrate an embodiment for multi-function surgical instrument 200, which includes a shaft 280 within it, where a grasper/forceps device has been attached to the distal end of the shaft 280. Therefore, in this embodiment for surgical instrument 200, the snare loop capability has been exchanged for a grasper/forceps capability. The grasper/forceps 370 is attached to the distal end of shaft 280 and thus is able to be extended from, and retracted into, bipolar electrode assembly 220 through movement of shaft 280 within catheter 208.

The grasper/forceps device 370, as was previously described for snare 270, can be attached to the distal end of shaft 280 through any of a variety of methods and the present invention is not limited to any particular method of attachment between grasper/forceps 370 and shaft 280. All that is required is that grasper/forceps 370 be attached to shaft 280 such that as shaft 280 is withdrawn into bipolar electrode assembly 220, the grasper/forceps 370 is also retracted within bipolar electrode assembly 220. As the grasper/forceps 370 is retracted into the bipolar electrode assembly 220, the engagement of the fingers 372 of the grasper/forceps 370 with the structure defining the lumen in bipolar electrode assembly 220 will collapse the fingers 372 and converge the fingers 372 together such that they are able to grasp tissue within the body of a patient.

As was discussed previously, where the snare loop could be configured in any of a variety of geometric shapes, the grasper/forceps 370 can also be formed in a variety of different configurations. FIGS. 19–24 illustrate several of the different configurations that could be utilized for grasper/forceps 370. As can be seen in FIG. 19, grasper/forceps 370 is comprised of three fingers 372. Each finger 372 includes a hook 374 at the distal end of the finger. The hook is provided to provide additional grasping capability to the grasper/forceps 370. FIGS. 20–24 provide front views of several of the various alternative configurations that could be utilized for the grasper/forceps 370. FIGS. 20–24 illustrate configurations 370A through 370E, respectively, for the grasper forceps 370. As can be seen, the grasper/forceps 370 can include any number of fingers with any relative positioning of the fingers within the grasper/forceps 370.

FIGS. 25 through 36 illustrate several additional embodiments for the surgical instrument of the present invention. As illustrated, other surgical tools could be included in the surgical instrument to provide additional capabilities to the multi-function surgical instrument 200.

Figures 25, 26:
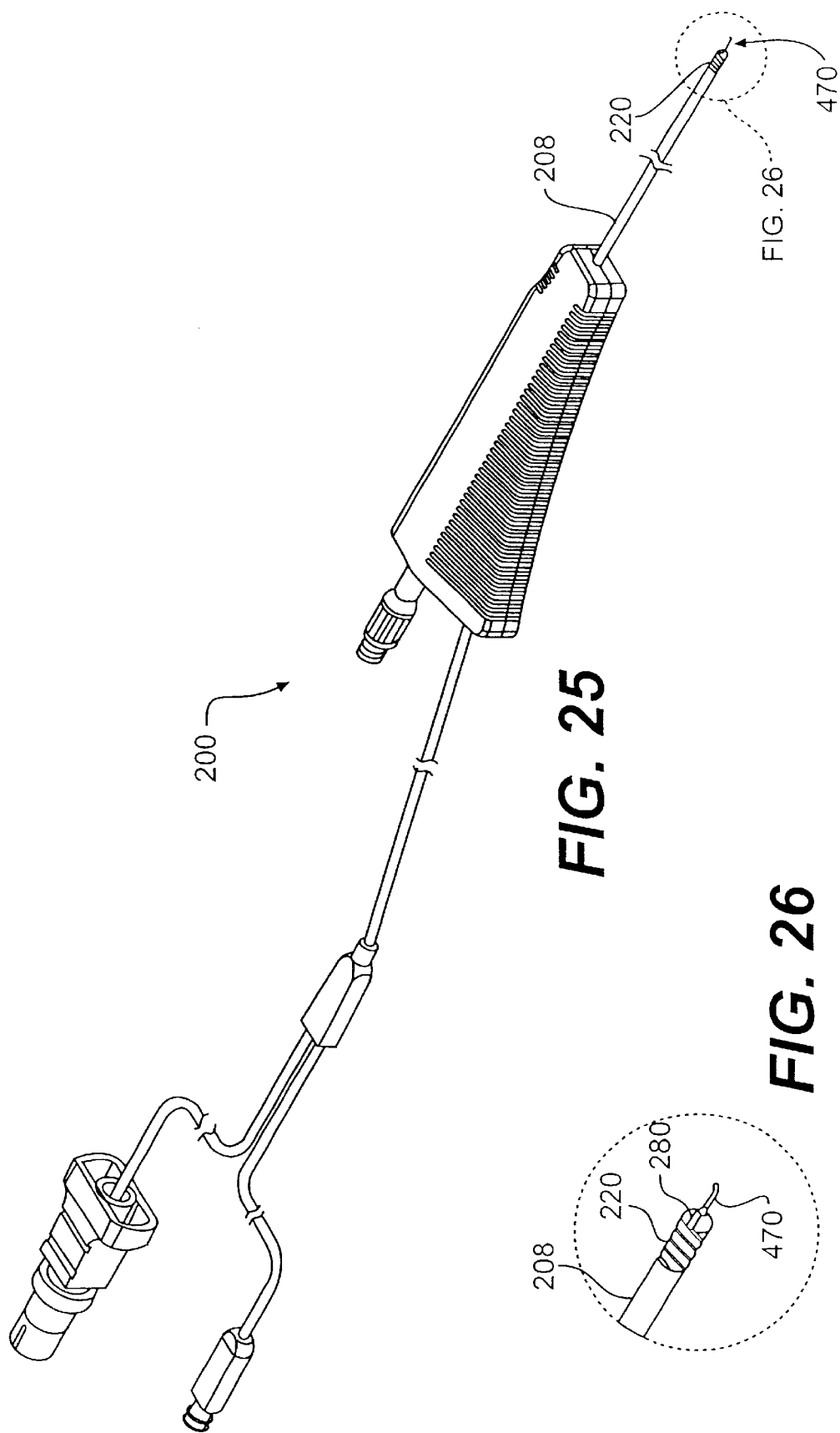
FIG. 25 illustrates an alternative embodiment for the multi-function surgical instrument of the present invention where a scraper/forceps device is attached to a support member.
FIG. 26 is a view of the distal end of the instrument of FIG. 25.

As is illustrated in FIGS. 25 and 26, a scraper/forceps device 470 is attached to the distal end of shaft 280. Again, the scraper/forceps 470 would be extended from bipolar electrode assembly 220 by distally moving shaft 280 within catheter 208 and scraper/forceps 470 would be retracted into the bipolar electrode assembly by proximally moving shaft 280 within catheter 208. Again, the scraper/forceps 470 could be manufactured from any of a variety of materials and can be attached to shaft 280 by any of a variety of attachment methods.

Additionally, scraper/forceps 470 can be configured in any of a variety of physical configurations. FIGS. 27 and 28 illustrate a first possible configuration for a scraper/forceps device. As can be seen in FIGS. 27 and 28, scraper/forceps 470A is comprised of a single finger 472A which includes a scraper portion 474A at its distal end. FIGS. 29 and 30 illustrate a second possible configuration for the scraper/ forceps and illustrates the scraper/forceps 470B as a single, elongated, cylindrical structure. FIGS. 31 and 32 illustrate a third possible configuration for a scraper/forceps device. In the embodiment of FIGS. 31 and 32, scraper/forceps 470C is comprised of a first finger 472C and a second finger 473C. First finger 472C includes a scraper portion 474C at its distal end and second finger 473C includes a scraper portion 475C at its distal end. FIGS. 33 and 34 illustrate a fourth possible configuration for a scraper/forceps device where scraper/ forceps 470D is comprised of four fingers, namely fingers 472D, 473D, 474D, and 475D. Each finger includes a scraper portion at a distal end thereof.

FIG. 35 illustrates an embodiment for surgical instrument 200 where a retrieval basket 570 has been attached to the distal end of shaft 280. The retrieval basket can be formed in any of a variety of configurations and would be retracted into, and extended from, bipolar electrode assembly 220 through movement of shaft 280 as previously described. Retrieval basket 570 could be utilized in accordance with well-known principles to capture a foreign body from within the body of a patient. The combination bipolar electrode assembly 220 and retrieval basket 570 would provide a single device to control bleeding from a foreign body while using the basket to remove the foreign body. Another use would be polyp or tissue retrieval after polypectomy or mucosectomy when the bipolar electrode assembly is used to treat post-procedural bleeding. The basket can also assist in adherent clot removal prior to cautery.

FIG. 36 illustrates an embodiment for surgical instrument 200 where a cytology brush 670 has been attached to the distal end of shaft 280. The cytology brush 670 would be used in accordance with well-known principals, e.g., for sampling for H Pylori before or after ulcer cautery.

FIG. 37 illustrates an embodiment for the multi-function surgical instrument where a balloon 770 has been added to the outside diameter of the catheter main shaft 208. The balloon 770 is disposed on the outside diameter of the catheter 208 and in a proximal direction with respect to bipolar electrode assembly 220. In order to provide for inflation and deflation of balloon 770, a balloon hub 772, as illustrated in FIG. 38, would be provided at the proximal end of the surgical instrument and could be provided as an extrusion off of the catheter main shaft 208. A lumen could be provided from the balloon hub 772, either through the main catheter shaft 208 or external to the main catheter shaft 208, to extend to balloon 770 for inflation and deflation of balloon 770. It should be understood that a balloon device 770 as illustrated in FIG. 37 could be utilized with any of the other previously discussed embodiments for the multi-function surgical instrument.

FIG. 39 illustrates an embodiment for surgical instrument 200 where shaft 280 is a hollow, tube structure and comprises a cryotherapy tube. The cryotherapy tube 870 extends through the lumen included in bipolar electrode assembly 220 and can be used to provide any of a variety of different gases 875, e.g., nitrous oxide, liquid nitrogen, or other gases for freezing and ablating tissue, within the body of the patient. The cryotherapy tube 870 can be extended from the bipolar electrode assembly 220 and retracted into the bipolar electrode assembly 220.

The above-described embodiments illustrate that a variety of different surgical tools can be incorporated into the multi-function surgical instrument of the present invention. Whereas a variety of these different types of surgical tools have been described, it can be contemplated that the multi-function surgical instrument can include any of a variety of other surgical tools. The additional surgical tools could be attached to either an injection needle assembly or an attachment member as was described herein. Thus, the present invention is not limited to only incorporating the tools as described herein in the multi-function surgical instrument. It is evident that one skilled in the art could contemplate other surgical tools being incorporated into the multi-function surgical instrument of the present invention and the teachings of the present invention could be utilized to implement these tools in the surgical instrument.

Additionally, it is not required that the hemostat assembly be a bipolar hemostat. The present invention can be practiced with a monopolar hemostat. The monopolar hemostat would include an aperture that would extend axially therethrough and which would accommodate a surgical tool within it.

As discussed above, the disclosed embodiments are illustrative of the various ways in which the present invention may be practiced. Other embodiments can be implemented by those skilled in the art without departing from the spirit and scope of the present invention.

What is claimed is:

1. A method for performing a surgical procedure on tissue within the body of a patient comprising the steps of:

inserting a catheter into the patient's body, the distal end of said catheter including a bipolar electrode assembly and said bipolar electrode assembly including an aperture extending longitudinally therethrough;

extending a distal end of an attachment member through said aperture included in said bipolar electrode assembly, wherein said attachment member is an injection needle and said attachment member includes a surgical tool attached to the distal end of said attachment member; and performing a surgical procedure on tissue of the patient with said surgical tool.

2. The method of claim 1 further comprising the step of performing a second surgical procedure on the tissue of the patent with said injection needle.

3. The method of claim 1 wherein said surgical tool is a snare.

4. The method of claim 1 further comprising the step of irrigating the tissue of the patient with irrigation fluid, said irrigation fluid provided to the tissue through said aperture included in said bipolar electrode assembly.

5. The method of claim 1 wherein said surgical tool is adapted to grasp patient tissue and said surgical procedure comprises the step of grasping the tissue of the patient.

6. The method of claim 1 wherein said surgical tool is adapted to scrape patient tissue and said surgical procedure comprises the step of scraping the tissue of the patient.

7. The method of claim 1 wherein said surgical tool is adapted to perform cryotherapy on patient tissue and said surgical procedure is cryotherapy.

8. The method of claim 1 wherein said surgical tool is a cytology brush.

9. The method of claim 1 further comprising the step of inflating a balloon, said balloon disposed on an outside diameter of said catheter at the distal end of said catheter.

10. The method of claim 1 wherein said surgical tool is a retrieval basket.

\* \* \* \* \*